United States Patent [19]

Dombek

[11] Patent Number: 4,540,712
[45] Date of Patent: Sep. 10, 1985

[54] PROCESS FOR PRODUCING METHANOL FROM SYNTHESIS GAS

[75] Inventor: Bernard D. Dombek, Charleston, W. Va.

[73] Assignee: Union Carbide Corporation, Danbury, Conn.

[21] Appl. No.: 563,270

[22] Filed: Dec. 20, 1983

Related U.S. Application Data

[63] Continuation of Ser. No. 372,412, Apr. 27, 1982, abandoned, which is a continuation of Ser. No. 135,775, Mar. 31, 1980, abandoned.

[51] Int. Cl.$^3$ .................. C07C 27/06; C07C 31/04
[52] U.S. Cl. .................................. 518/700; 502/150
[58] Field of Search ............................. 518/700

[56] References Cited

U.S. PATENT DOCUMENTS

| | | |
|---|---|---|
| 2,535,060 | 12/1950 | Gresham . |
| 2,549,470 | 4/1951 | Howk et al. . |
| 2,632,014 | 3/1953 | Gresham . |
| 3,579,566 | 5/1971 | Fenton . |
| 3,833,634 | 9/1974 | Pruett et al. . |
| 4,153,623 | 5/1979 | Kaplan et al. . |
| 4,162,261 | 7/1979 | Kaplan . |
| 4,170,605 | 10/1979 | Williamson et al. . |
| 4,189,441 | 2/1980 | Braca et al. . |
| 4,268,689 | 5/1981 | Knifton, III . |
| 4,270,015 | 5/1981 | Knifton . |

FOREIGN PATENT DOCUMENTS

| | | |
|---|---|---|
| 2644185 | 4/1977 | Fed. Rep. of Germany . |
| 2024811 | 1/1980 | United Kingdom . |

OTHER PUBLICATIONS

Catalytic Letters, vol. 5, No. 1, Jan. 1979.

*Primary Examiner*—Howard T. Mars
*Attorney, Agent, or Firm*—Bernard Francis Crowe

[57] ABSTRACT

This invention relates to the manufacture of methanol directly from the liquid phase reaction of hydrogen and carbon monoxide, by a homogeneous catalytic process using as the catalyst a solubilized ruthenium carbonyl complex and a promoter for said reaction in the liquid phase.

15 Claims, No Drawings

PROCESS FOR PRODUCING METHANOL FROM SYNTHESIS GAS

This application is a continuation of application Ser. No. 372,412, filed Apr. 27, 1982, which in turn is a continuation of aplication Ser. No. 135,775, filed Mar. 31, 1980, both of which are abandoned.

BACKGROUND OF THE INVENTION

This invention relates to a catalytic process for producing methanol directly from synthesis gas. more particularly, the invention concerns reacting synthesis gas, i.e., mixtures of hydrogen and carbon monoxide, in the presence of a stable ruthenium carbonyl complex catalyst to directly form methanol.

Methanol is an increasingly important feedstock for the production of carbon-based chemicals. Existing or proposed commercial processes using methanol include dehydrogenation to form formaldehyde, carbonylation to form acetic acid, homologation to form ethanol and reactions over zeolitic materials to form gasoline grade fractions. Owing to the reduced availability of petroleum, the cost of producing chemicals from petroleum has been steadily increasing and the anticipated increase in commercial methanol manufacture has underscored the need for a different, low cost source which can be converted into chemicals.

Synthesis gas, which is derived by the combustion of any carbonaceous material including coal, or any organic material, such as hydrocarbons, carbohydrates and the like has for a long time been considered a desirable starting material for the manufacture of a variety of chemicals. Hydrocarbons have been made by the Fischer-Tropsch catalytic reaction. Methanol is commercially manufactured by a heterogeneous catalytic reaction from synthesis gas. Aldehydes and alcohols are made from the reaction of olefins and synthesis gas.

One of the deficiencies of known processes for making chemical products from synthesis gas involves the use of heterogeneous catalysts or, when using a homogeneous catalytic reaction, employing a rhodium carbonyl complex catalyst which is extemely expensive. Rhodium is employed in auromotive catalytic converters which comprise the combustion devices for reducing automotive pollutant emissions. The high cost of rhodium is created by its limited availability and the tremendous demand for it. Thus, a commercial process which uses rhodium as a catalyst is affected by the high capital expense to purchase the metal and the strict controls needed to limit catalyst losses in order to keep the economics of the process competitive.* Ruthenium, on the other hand, is a precious metal which has no significant commercial application. Its present cost is approximately 1/20th, and less, that of rhodium even through its concentration in the ore from which both are obtained is about the same.

* See Cornils, et al., Hydrocarbon Processing, June, 1975, pp. 83 to 91.

Ruthenium has been explored as a catalyst by many. It has been considered as a hyrogenation catalyst, as an alcohol homologation catalyst, as a catalyst to produce a wide range of monohydric alcohols (non-specific as to any of them) exclusive or methanol, as an alcohol homologation catalyst such as for the conversion of methanol to ethanol,** and as a high pressure catalyst to selectively produce methanol and methyl formate.

** See, for example U.S. Pat. Nos. 4,133,966 and 3,285,948; and Japanese patent application (Kokai) No. 52-73804/77 (June 21, 1977) [application No. 50-149391/75 (application date, Dec. 15, 1975)] to Mitsubishi Gas Chemical Industry Company.

For example, in a recent report (Journal of the American Chemical Society, vol. 101, pp. 7419-21 (1979)) J. S. Bradley of Exxon Corporation produced methanol and methyl formate at a selectivity greater than 99% without hydrocarbon products detected, by the reaction of synthesis gas ($H_2$:CO=2:1) under pressures on the order of 1,300 atmospheres and at temperatures around 270° C. using a Ru catalyst, which under the conditions of the reaction was present as $Ru(CO)_5$. Bradley reported that no homologation products were found.

In Willismson, et al., U.S. Pat. No. 4,170,605, patented Oct. 9, 1979, the patentees report in Examples I and II the reaction in 1-propanol of synthesis gas (CO:$H_2$=1:1) at 25,000 psig and at 230° C. using ruthenium tris(acetylacetonate) and 2-hydroxypyridine for a period of 2 and 3 hours, respectively. In Example I, Williamson, et al. report the production of 4 grams of product*.containing (mole percent basis): ethylene glycol, 57; and methanol, 25. In Example II, 7 grams of product* are reported containing 66 and 16 mole percent of ethylene glycol and methanol, respectively.

* Included in the 4 and 7 grams of product are trace amounts of water and methylformate, as well as 16 mole % (Example I) and 15 mole % (Example II) of propylformate. The latter compound would appear to be derived form 1-propanol initially present in the reaction mixture, rather than a synthesis gas-derived product.

Further, in copending application Ser. No. 91,242, filed Nov. 15, 1979, now abandoned in favor of continuing application Ser. No. 319,887, filed Nov. 10, 1981; Ser. No. 358,703, filed Mar. 16, 1982 and Ser. No. 359,778, filed Mar. 19, 1982, there is described a process for selectively producing methanol, ethanol, and ethylene glycol by reacting carbon monoxide and hydrogen in a homogeneous liquid phase mixture containing a ruthenium carbonyl complex. The reaction is effected at a temperature between about 50° C. to about 400° C. and a pressure of between about 500 psia (35.15 kg/cm$^2$) and about 15,000 psia (1,054.6 kg/cm$^2$) for a period of time sufficient to produce such products; and in U.S. Pat. No. 4,323,513, there is described an improved process for producing methyl and ethylene glycol esters as described in U.S. Ser. No. 91.242 in which the improvement comprises maintaining the combined concentration of methyl ester, ethylene glycol ester and water in the reaction medium at less than about 30 vol. %.

Thus, while previously known processes using homogeneous ruthenium catalysts will produce methanol with high selectivity, generally very high pressures are required or other products are also produced and it would be desirable to produce only methanol or derivatives thereof at high process efficiency and low or moderate pressures.

SUMMARY OF THE INVENTION

In accordance with the present invention there is provided a process for making methanol, or derivative precursors such as acylates, directly from the reaction of hydrogen and carbon monoxide. The process comprises:

(a) establishing and maintaining a solvent-containing liquld phase comprising solubilized ruthenium carbonyl complex in which the solvent has a dielectric constant of at least 2, determined at 25° C. or at its melting point, whichever is higher;

(b) supplying hydrogen and carbon monoxide in said liquid phase;

(c) providing a promoter of said reaction in said liquid phase; and (d) maintaining said liquid phase for a sufficient period of time at a temperature and pressure which causes said hydrogen and carbon monoxide to react to produce methanol, said temperature is between about 50° C. and 400° C. and said pressure is between about 500 psia (35.15 kg/cm$^2$) and 15,000 psia (1,054.6 kg/cm$^2$).

The catalyst of this invention is that catalyst which is formed during the course of the reaction.

The process of this invention involves the conversion of synthesis gas, however derived, into large amounts of methanol which can be directly consumed or which can be employed as starting materials to make other valuable chemicals. The process of this invention is capable of producing methanol in high concentrations with substantially no other alcohol or undesirable by products being prepared. Moreover, the process of this invention provides the capability of a low cost route to methanol.

DESCRIPTION OF THE INVENTION

This process constitutes a relatively low pressure process for converting synthesis gas to methanol. The process of this invention is carried out with the ruthenium carbonyl complex dissolved in a solvent, even though such complex may exist during the reaction in more than one liquid phase. In this sense, the reaction is termed a homogeneous liquid phase reaction. There may be more than one such phase existing in rhe reaction zone but the ruthenium carbonyl complex existing as the catalyst is always dissolved in at least one of such phases and is always in a dissolved liquid state. The problem with heterogeneous ruthenium catalysis in the reaction zone is that such will induce the Fischer-Tropsch reaction resulting in the formation of hydrocarbons and/or a variety of oxygenated hydrocarbons having a variety of molecular weights with low selectivity to any one compound. In fact the presence of such products suggests that undissolved ruthenium is present.

The process of this invention involves the reaction of soluble ruthenium complexes in the presence of Lewis-acid promoters with synthesis gas at temperatures, pressures and for a period of time sufficient to produce methanol. Such conditions are set forth herein. The reaction conditions comprise (i) a period of time at a temperature and pressure which cause the hydrogen and carbon monoxide to react to produce the desired product, (ii) a temperature between about 50° C. and 400° C. and (iii) a pressure between 500 psia (35.15 kg/cm$^2$) and 15,000 psia (1,054.6 kg/cm$^2$). The catalyst of this invention is the ruthenium containing carbonyl complex which under the prescribed reaction conditions catalyzes the aforementioned reaction between carbon monoxide and hydrogen.

The process of this invention is distinctive in the selection of materials which comprise the homogeneous liquid phase mixture, the reaction parameters and the stability of the ruthenium containing catalyst in most cases, indeed, in all cases studied. As with any technology, this process has undergone evolutionary changes and its further examination will undoubtedly bring about more changes, most likely in the form of additional or substitutional steps and/or materials.

In accordance with the invention the process is carried out in the presence of a promoter. A promoter, in the context of this invention, is a material provided to the reaction which provides a promotional effect in that it enhances the production (viz., rate, yield or efficiency) of methanol or it helps to reduce the loss of ruthenium during the reaction. The promoter may be any Lewis acid containing compound. Any Lewis acid may be a promoter but all Lewis acids will not serve to act as a promoter under any given set of reaction conditions. The effectiveness of the Lewis acid as a promoter will in large measure be dependent upon the reaction conditions selected. Operation of the process in the absence of the Lewis acid promoter will result in less productivity and therefore, exploitation of the process in a commercial sense will necessitate the use of the promoter.

The amount of Lewis acid promoter added to the process is that amount which provides the promotional effect. The maximum amount employed is that amount whose presence is too costly for the economical operation of the process, or substantially reduces the promotional effect without any advantage, or provides no advantage in the operation of the process, or a combination of these factors. The promoter can be a material used in miniscule quantities to a material employed in maximum quantities such as a solvent for the reaction and the ruthenium carbonyl complex catalyst. The promoter can also be a material which when present reacts with the products of the reaction.

Apart from the conditions of the reaction in terms of time, temperature and pressure, the selection of solvent and Lewis acid promoter constitute important considerations in the most advantageous practice of this invention. The selections of solvent and promoter are not narrowly limited yet there appears to be some degree of cooperation that each imparts to the success of the process and the selection of one oftentime dicatates the selection of the other in order to maximize the benefits of the invention.

It is found necessary that there be used a solvent that is capable of maintaining the chosen ruthenium carbonyl complex and the Lewis acid promoter (if it is not the solvent), in the homogeneous liquid phase mixture throughout the reaction. This appears to be the prime function of the solvent. The solvent may possibly provide an additional benefit such as influencing the kinds of ion pairing that exist during the course of the reaction.

The catalyst of this invention is a ruthenium compound which contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such as ruthenium salts, oxides and carbonyl clusters may be introduced to the reaction in a condition which allows them to be solubilized, and under the conditions of the reaction they are converted into a carbonyl complex which effectively catalyzes the reaction. That is why they are defined in terms of products made by the process. The composition and structure of the ruthenium carbonyl complex which catalyzes the desired reaction is not specifically known. Factors in achieving the catalyst are the reaction parameters, the choice of solvent, and the Lewis acid promoter that one employs. Because varied reaction conditions, solvents, and promoters, result in different amounts of the desired product of the process, and different rates, efficiencies and/or yields, it is presumed that each provides a different and distinct catalytic environment.

The ruthenim-containing substance which may be employed in the practice of this invention to form the catalyst under process conditions encompass those which are described, for example, in Gresham, U.S. Pat. No. 2,535,060 at column 2, starting at line 38 to line 48, and ruthenium carbonyl compounds. It is not advisable to place ruthenium compounds or substances on a support material for use in the process of this invention because such offers no benefits over solubilizing such ruthenium compounds in combination with the aforementioned solvent and Lewis acid promoter. Moreover, ruthenium deposited on a support material can be expected to be solubilized in the homogeneous liquid phase reaction system of this invention as it is contacted with carbon monoxide. Even ruthenium metal in the presence of the solvent, carbon monoxide and hydrogen can be converted to a ruthenium carbonyl complex which is soluble. Ruthenium oxides, such as dioxide, sesquioxide, or tetraoxide, are capable under appropriate conditions of being solubilized and converted to a carbonyl complex which can be used to form the catalyst under the conditions of this process. However, when using such insoluble ruthenium compounds, they must first be solubilized before the effective operation of the process of this invention. Ruthenium carbonyl compounds (which include ruthenium carbonyl or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than other ruthenium compounds. On that basis, one can select for the purposes of convenience the particular ruthenium compound to be utilized in forming the catalyst. However, ruthenium which is associated with an organic molecule or complexed with carbon monoxide is most readily solubilized so as to provide the ruthenium catalyst of this process.

As characterized above, this process is operated as a homogeneous liquid phase mixture. The process is typically carried out in a solvent for the catalyst and the Lewis acid promoter. Thus the solvent is a liquid in which the catalyst (presumed to be a ruthenium carbonyl complex) and the added Lewis acid promoter are soluble under the prescribed conditions of the reaction. The solvent may be solid at room temperature but should at least in part be a liquid under the conditions of reaction.

Illustrative of suitable solvents are, e.g., water, alcohols, ketones, esters including lactones, amides including lactams, sulfones, sulfoxides, halogenated hydrocarbons aromatic hydrocarbons, and the like. Illustrative of specific slovents encompassed by the above classes of polar solvents are, for example, aromatic hydrocarbons, e.g., benzene, toluene, xylene, naphthalene, alkynaphthalene, etc.; carboxylic acids such as acetic acid, propionic acid, butyric acid, caprioc acid, stearic acid, benzoic acid, cyclohexanecarboxylic acid, etc., see the description of acyl compounds in Ser. No. 971,667 filed Dec. 21, 1978, abandoned in favor of the previously mentioned continuation-in-part application Ser. No. 91,242, filed Nov. 15, 1979; alcohols such as methanol, ethanol, n-butanol. etc.; ketones such as acetone, methylethyl ketone, cyclohexanone, cyclopentanone, etc.: esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactam, such as N-methylcaprolactam, N-alkyl pyrrolidinones such as N-methyl pyrrolidinone: cyclic ureas such as N,N-dimethylimidazolidone polyols such as ethylene glycol, glycerine, erythritol, polyalkylene glycol containing two to about ten thousand repeating units; lactones such as gamma-butyrolactone; halogenated hydrocarbons such as chlorobenzene, chloroform, methylene chloride, 2,2-dichloropropane; amides such as dimethylformamide, dimethylacetamide, hexamethylphosphoramide; sulfones such as sulfolane, dimethylsulfone, the substituted sulfolanes described in U.S. Pat. No. 4,224,237; sulfoxides such as dimethylsulfoxide, diphenyl sulfoxide; as well as many other.

Other suitable solvents are the ethers, cryptands, and the like. Illustrative of specific solvents encompassed by the above classes of solvents are, for example, ethers such as tetrahydrofuran, tetrahydropyran, diethyl ether, 1,2-dimethoxybenzene, 1,2-diethoxybenzene, the mono and dialkyl ethers of alkylene and polyalkylene glycols, such as ethylene glycol, of 1,2-propylene glycol, of 1,2-butylene glycol, of diethylene glycol, of di-12,2-propylene glycol, of triethylene glycol, of pentaethylene glycol (such as triglyme, tetraglyme and pentaglyme), of di-1,2-butylene glycol, of oxyethyleneoxypropylene glycols, etc., preferably those in which the alkylene group contains 2 and/or 3 carbon atoms in the divalent moiety, such as ethylene and 1,2-propylene; the cryptands such as described in U.S. Pat. No. 4,111,975, which description of cryptands, as promoters in that case, are incorporated herein by reference; the crown ethers (or Crown Ethers, as one may prefer) such as described in U.S. Pat. No. 4,162,261, which description of crown ethers, as solvents in that case, are incorporated herein by reference; as well as many others.

The choice of solvent in any particular case can be a complex decision. Some solvents such as the carboxylic acids (e.g., acyl compounds described in U.S. patent application Ser. No. 971,667) play a dual role in the practice of the process of this invention. They can provide the required Lewis acid promoter as well as the solvent. In many instances, solvents react with the product of the reaction and such reactive solvents are considered useful in the practice of this invention because the derivative products obtained are an excellent source for the desired products of the reaction. For example, the carboxylic acids are not only effective solvents and promoters, they are also reactive with the methanol product, to produce methyl carboxylate which can be readily hydrolyzed to produce the alcohol product.

The Lewis acids suitable as promoters in the practice of this process are not a narrowly defined class of materials. They encompass a broad range of inorganic and organic materials, and all members of the class are contemplated as employable in the practice of this invention. Its effectiveness in some instances can be noted when used in as little an amount which is the least amount that a measurable promotional effect is seen to an amount wherein the Lewis acid is also a solvent for the reaction. The Lewis acid can serve a dual function by playing the role as the solvent for the reaction. There is no simple way of determining what Lewis acid will function effectively under a given set of reaction conditions. In the typical case, when a Lewis acid exhibits promotional affects on the rate of the reaction, it is present and dissolved in the liquid phase in a range of from about 0.01 mole to about $10^6$ moles for each atom (gram atomic weight) of ruthenium present in the reaction. More preferred, the Lewis acid is present (even when the solvent used is a Lewis acid) in the liquid phase in a range from about 1 mole to about $10^4$ moles for each atom of ruthenium present in the reaction; most preferably, greater than one mole up to about 1000 moles of the Lewis acid for each atom of ruthenium present and dissolved in the liquid phase.

The Lewis acid promoters include inorganic as well as organic compounds, which (as defined by G. N. Lewis, J. Franklin Inst., Vol. 226. p. 293 (1938) are compounds which are capable of acting as electron pair acceptors.

Suitable Lewis acid promoters for the process of this invention include salts containing alkali metal cations, such as $NaPF_6$, $KBF_4$, and $CsCl$; salts containing alkaline earth metal cations, such as $MgCl_2$ and $CaI_2$; salts of zinc, cadmium, and mercury, such as $ZnCl_2$ and $HgI_2$; compounds of boron, such as $B(OH)_3$, $B(OCH_3)_3$, and $BF_3$; compounds of aluminum and gallium, such as $Al(OH)_3$, $Al(OCH_2CH_3)_3$, $GaCl_3$, and $Ga(OH)_3$ oxo acids, such as $H_3PO_4$ and $CH_3CO_2H$; and binary acids such as HF and HCl, as well as many others.

Not all of the above Lewis acids, or for that matter all Lewis acids, will necessarily function effectively in all of the embodiments of the process of this invention. In most cases a degree of selection between the choice of Lewis acid, the amount of ruthenium, the choice of solvent and the reaction parameters will be required to obtain the level of productivity sought.

Because $H_2$ is supplied to the reaction, a hydride of ruthenium can exist in the reaction system but there is no appreciation of the particular role that the hydride is playing in the reaction.

The relative amounts of carbon monoxide and hydrogen which are initially present in the reaction mixture can be varied over a wide range. In general, the molar ratio of $CO:H_2$ is in the range of from about 40:1 to about 1:40, suitably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. Mixtures of carbon dioxide, carbon monoxide and hydrogen can also be employed. If desired, the reaction mixture can comprise steam and carbon monoxide.

The quantity of catalyst employed is not narrowly critical and can vary over a wide range. In general, the process is desirably conducted in the presence of a catalytically effective quantity of the active ruthenium species which gives a suitable and reasonable reaction rate. Reaction can proceed when employing as little as about $1 \times 10^{-6}$ weight percent, and even lesser amounts, of ruthenium based on the total weight of reaction mixture (i.e., the liquid phase mixture). The upper concentration limit can be quite high, e.g., about 30 weight percent ruthenium, and higher, and the realistic upper limit in practicing the invention appears to be dictated and controlled more by economics in view of the cost of ruthenium. Since the rate of conversion of synthesis gas may be dependent upon the concentration of ruthenium employed, higher concentrations achieving higher rates, then large concentrations may prove to be a most desirable embodiment of this invention. Depending on various factors such as the Lewis acid promoter, the partial pressures of carbon monoxide and hydrogen, the total operative pressure of the system, the operative temperature, the choice of solvent, and other considerations, a catalyst concentration of from about $1 \times^{-3}$ to about 20 weight percent ruthenium (contained in the complex catalyst) based on the total weight of reaction mixture, is generally desirable in the practice of the invention.

The temperature which may be employed in practicing the process may vary over a wide range of elevated temperatures. In general, the process can be conducted at a temperature between about 50° C. and about 400° C. and higher. Temperatures outside this stated range, though not excluded from the scope of the invention, do not fall within certain desirable embodiments of the invention. At the lower end of the temperature range, the rate of reaction to desired product becomes markedly slow. At the upper temperature range, and beyond, catalyst, solvent, or Lewis acid promoter instability will continue and the methanol and/or its derivatives will be produced. Preferred temperatures are between about 100° C. and about 350° C., and most desirably, between about 150° C. and about 300° C.

The process is suitably effected over a wide superatmospheric pressure range. At pressures in the direction of and below about 500 psia (35.15 kg/cm²), the rate of desired product formation is quite slow, and consequently, relatively faster reaction rates and/or higher conversions to the desired products can be obtained by employing higher pressures, e.g., pressures of at least about 1,000 psia (70.31 kg/cm²). Pressures as high as 20,000 to 50,000 psia (3,515.35 kg/cm²), and higher, can be employed but there is no apparent advantage in using such pressures, and any advantage that could be reasonably contemplated be easily offset by the very unattractive plant investment outlay required for such high pressure equipment and the costs associated with such high pressure operations. Therefore, the upper pressure limitation is approximately 15,000 psia (1,054.6 kg/cm²). Effecting the process below about 15,000 psia (1,054.6 kg/cm²), especially below about 10,000 psia (703.1 kg/cm²), results in significant cost advantages which are associated with lower pressure equipment requirement and operating costs. A suitable pressure range is from about 500 psia (35.15 kg/cm²) to about 12,500 psia (878.84 kg/cm²). The pressures referred to above represent the total pressure of hydrogen and carbon monoxide.

The process is effected for a period of time sufficient to produce the methanol product and/or derivatives thereof. In general, the residence time to produce the desired product can vary from minutes to a number of hours, e.g., from a few minutes to 24 hours, and longer. It is readily appreciated that the residence period (time) will be influenced to a significant extent by the reaction temperature, the concentration and choice of Lewis acid promoter and ruthenium source, the total gas pressure and the partial pressure exerted by its components, the concentration and choice of solvent, and other factors. The synthesis of the desired product by the reaction of hydrogen with carbon monoxide is suitably conducted under operative conditions which give reasonable reaction rates and/or conversions.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst precursor may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the process especially to maintain the desired molar ratios of and the partial pressures exerted by the reactants.

As intimated previously, the operative conditions can be adjusted to optimize the conversion of the desired product and/or the economics of the process. In a continuous process, for instance, when it is preferred to operate at relatively low conversion, it is generally desirable to recirculate unreacted synthesis gas with/without make-up carbon monoxide and hydrogen to the reactor. Recovery of the desired product can be achieved by methods well-known in the art such as by distillation, fractionation, extraction, and the like. A fraction comprising ruthenium complex, generally contained in byproducts and/or the solvent, can be recycled to the reaction zone, if desired. All or a portion of such fraction can be removed for recovery of the ruthenium values or regeneration thereof, if necessary. Fresh ruthenium precursor, Lewis acid promoter and/or solvent, can be intermittently added to the recycle stream or directly to the reaction zone, if needed.

Many embodiments of the ruthenium carbonyl complex, Lewis acid promoter, and solvent combinations encompassed by this invention are sufficiently stable to allow repeated use of the ruthenium carbonyl complex. For example, the process of this invention can be continuously operated in a pressure reactor into which is continuously fed synthesis gas. The velocity of the synthesis gas is sufficient to strip products of the reaction out of the reactor leaving behind in the reactor the ruthenium carbonyl complex, Lewis acid and solvent combination. The products are separated from the unreacted synthesis gas and the synthesis gas is recycled to the reactor. The products, in this embodiment, are recovered free of ruthenium, Lewis acid and solvent. In this embodiment, the catalyst need not be removed from the reactor to a recovery zone for separating product. Thus a catalyst treatment step is avoided. The examples below depict batch reactions; however, the above continuous gas recycle process can be operated in a similar manner. That is, the batch reactor simulates the continuous reactor except for the gas sparging and continous gas recycle.

Although this invention has been described with respect to a number of details, it is not intended that this invention should be limited thereby. Moreover, the examples which follow are intended solely to illustrate a variety of, including the most favorable, embodiments of this invention and are not intended in any way to limit the scope and the intent of this invention.

EXAMPLES

In examples 1–9, recorded in Table I below, the following procedure was employed:

A 500 ml stainless steel bomb reactor containing a removable glass liner was charged with a mixture of 0.50 g $Ru_3(CO)_{12}$ (2.35 mmoles Ru), solvent and Lewis acid as designated below. Carbon monoxide and hydrogen were then added in equimolar amounts to the reactor to attain a pressure therein of 3,000 psig 211.95 kg/cm$^2$) at 25° C. The reactor was rocked and the contents heated to the reaction temperature and maintained at this temperature for two hours (except when noted otherwise) while rocking the reactor. The reactor was then cooled and vented. The contents of the reactor were removed and analyzed by gas chromatography. No ethylene glycol or ethanol were detected by these analyses.

Examples 1, 2, 4, and 8 are comparison examples. Example 1 shows the low yield of methanol obtained by use of tetrahydrofuran solvent (as used by Bradley Supra) Examples 2 and 4 are to be used for comparison with the succeeding examples 3 and 5–7 respectively where Lewis acid promoters were used. Example 8 is for comparison with Example 9, which uses a Lewis acid promoter.

TABLE I

| Example | Promoter | Millimoles of Promoter | Solvent | Milliliters of Solvent | Reaction Temperature (°C.) | Methanol Produced (grams) |
|---|---|---|---|---|---|---|
| 1 | — | — | Tetrahydrofuran | 50 | 230 | 0.08 |
| 2 | — | — | Ethanol | 50 | 230 | 1.16 |
| 3 | Triethoxyaluminum | 43.2 | Ethanol | 50 | 230 | 1.78 |
| 4* | — | — | Ethanol | 50 | 250 | 2.40 |
| 5 | B(OH)$_3$ | 58.8 | Ethanol | 50 | 250 | 2.00 |
| 6 | B(OH)$_3$ | 161.3 | Ethanol | 50 | 250 | 2.96 |
| 7 | B(OH)$_3$ | 161.3 | 2-Propanol | 50 | 250 | 2.87 |
| 8 | — | — | Sulfolane | 50 | 230 | 0.57 |

TABLE I-continued

| Example | Promoter | Millimoles of Promoter | Solvent | Milliliters of Solvent | Reaction Temperature (°C.) | Methanol Produced (grams) |
|---|---|---|---|---|---|---|
| 9 | CsCl | 2.97 | Sulfolane | 40 | 230 | 1.06 |

*Reaction time was 2.75 hr.

EXAMPLE 10

A 500 ml stainless steel bomb reactor containing a removable glass liner was charged with a mixture of 1.0 g. $Ru_3(CO)_{12}$ (4.69 mmoles Ru) in 50 ml of ethyl acetate. Equimolar amounts of carbon monoxide and hydrogen were then added to the reactor to attain a pressure therein of 2,600 psig (182.8 kg/cm$^2$) at 25° C. The reactor was rocked and the contents heated to 250° C. and maintained at this temperature for four hours rocking the reactor. The reactor was then cooled and vented. The contents of the reactor were removed and analyzed by gas chromatography. This analysis showed that the following products were produced 2.30 grams of methanol and 3.33 grams of methyl acetate.

What is claimed is:

1. The process for making the products methanol or carboxylate derivatives thereof directly from synthesis gas mixtures consisting of hydrogen and carbon monoxide, which comprises;
   establishing and maintaining a solvent-containing liquid phase comprising solubilized ruthenium carbonyl catalyst complex in which the solvent has a dielectric constant of at least 2, determined at 20° C. or at its melting point, whichever occurs higher;
   supplying hydrogen and carbon monoxide to said liquid phase;
   providing a Lewis acid which is a compound of boron, aluminum or gallium, as promoter of said reaction in said liquid phase; and
   maintaining said liquid phase for a sufficient period of time at a temperature and pressure which causes said hydrogen and carbon monoxide to react to produce such products in high concentrations with substantially no by-products or other alcohols being prepared, wherein said temperature is between about 50° C. and 400° C. and said pressure is between about 500 psia (35.15 kg/cm$^2$) and 15,000 psia (1,054.6 kg/cm$^2$).

2. The process of claim 1 wherein the solvent is a carboxylic acid and the products formed are corresponding derivative carboxylates.

3. The process of claim 1, wherein the temperature is between about 100° C. and about 350° C.

4. The process of claim 1, wherein the pressure is between about 500 psia (35.15 kg/cm$^2$) and 12,500 psia (878.84 kg/cm$^2$).

5. The process of claim 1, wherein the pressure is the total pressure of hydrogen and carbon monoxide supplied to said process.

6. The process of claim 1, wherein the solvent is water.

7. The process of claim 1, wherein the solvent is an alcohol.

8. The process of claim 1, wherein the solvent is a carboxylate ester.

9. The process of claim 1, wherein the solvent is a sulfone.

10. The process of claim 1, wherein the solvent is an ether.

11. The process of claim 1 wherein the solvent is a crown ether.

12. The process of claim 1, wherein the solvent is acetic acid.

13. The process of claim 1 wherein the promoter is an aluminium containing compound.

14. The process of claim 1, wherein the promoter is a boron containing compound.

15. The process of claim 1, wherein the Lewis acid promoter is triethoxy aluminum or boric acid.

* * * * *